United States Patent [19]
O'Brien et al.

[11] Patent Number: 5,476,794
[45] Date of Patent: Dec. 19, 1995

[54] DETECTION METHOD FOR CHECKING SURFACES FOR NITROGEN-CONTAINING EXPLOSIVES OR DRUGS

[75] Inventors: Stephen E. O'Brien, Bolton; David H. Fine, Sudbury; Freemand W. Fraim, Lexington, all of Mass.

[73] Assignee: Thermedics Inc., Woburn, Mass.

[21] Appl. No.: 282,780

[22] Filed: Jul. 29, 1994

Related U.S. Application Data

[63] Continuation of Ser. No. 25,473, Mar. 3, 1993, abandoned, which is a continuation of Ser. No. 672,296, Mar. 20, 1991, abandoned.

[51] Int. Cl.⁶ .................................................... F42B 13/10
[52] U.S. Cl. .................... 436/92; 436/111; 436/107; 436/901; 436/156; 422/61; 73/1 G
[58] Field of Search ............................ 436/92, 156, 110, 436/111, 107, 901; 422/88–89, 61, 58; 55/67–68; 73/1 G

[56] References Cited

U.S. PATENT DOCUMENTS 3,672,351  6/1972  Ubersax et al. ..................... 422/58
4,909,090  3/1990  McGown et al. ..................... 73/864.33
5,092,218  3/1992  Fine et al. ............................. 55/67
5,092,219  3/1992  Rounbehler et al. ................. 55/67

Primary Examiner—Lyle A. Alexander
Attorney, Agent, or Firm—Darby & Darby

[57] ABSTRACT

Disclosed is a method of rapidly checking surfaces for the presence of traces of specific compounds such as certain explosives and drugs. A hand-covering such as a cotton glove is used to wipe surfaces to pick up particles of the specific compound which may indicate the presence of larger amounts or previous contact of a surface by a person who has handled the compound. The particles are transferred—unheated—to collection surfaces of a hand-held sample probe by vacuuming of the gloved hand by the battery-operated probe. Heat is then supplied by a source external to the probe to vaporize the particles, and the vapors are analyzed by a suitable technique such as high speed gas chromatography. The method permits checking of surfaces for explosives at processing rates of up to several samples per minute.

2 Claims, 6 Drawing Sheets

DETECTION METHOD FOR CHECKING SURFACES FOR NITROGEN-CONTAINING EXPLOSIVES OR DRUGS

This application is a continuation of application Ser. No. 08/025,473, filed Mar. 3, 1993, now abandoned, which in turn is a continuation of application, Ser. No. 07/672,296 filed Mar. 20, 1991, now abandoned.

BACKGROUND OF THE INVENTION

This invention relates to detection of compounds such as explosives by their presence on surfaces. In particular, it concerns collection of compounds by wiping of trace amounts from surfaces with hand-coverings followed by rapid analysis of the collected compounds.

Various methods are known for acquiring and analyzing samples in order to detect compounds such as explosives concealed in luggage or other containers and whose presence in trace amounts on surfaces may indicate contact by a person who has handled such compounds. For example, U.S. Pat. No. 4,909,090, assigned to the assignee of the present invention and whose disclosure is incorporated herein by this reference to that patent, discloses a hand-operable vapor sampling probe which in a surface sampling mode heats and directs jets of air onto surfaces to produce/dislodge vapors of drugs or explosives. The vapors are drawn over, and trapped on, collector surfaces in the probe, then are subsequently desorbed and analyzed.

Another technique, referred to in U.S. Pat. No. 4,788,039, involves use of dry filter paper as a sampling device to acquire samples, as by application of the filter paper against the fingertips of a person suspected of handling explosives. Two chemical reagents are then applied in succession to the filter paper to check for specific explosives.

Although the above-noted detection equipment and methods are useful, additional improvements in speed and flexibility are desirable for certain detection applications. For example, the use of a piece of filter paper or the sampling probe of U.S. Pat. No. 4,909,090 to check multiple objects of different sizes and shapes in a room would require considerable time and effort. Moreover, some surface portions of certain objects (e.g., a telephone, radio, door handle) could be incompletely sampled during normal use of the equipment and procedures described in these patents. These prior art techniques may thus be less than optimum where speed and completeness of sampling are of particular importance, as in high volume strategic areas such as airport terminals. In addition, a sampling probe which can both heat samples and puff and draw air over collector surfaces may be rather complex and bulky for ease of operation.

Accordingly, it is an object of the invention to provide an improved method for rapid checking of surfaces for the presence of specific compounds.

It is a particular object of the invention to provide a method for rapid, selective detection of trace amounts of explosives on surfaces.

It is an object of the invention to provide an improved method for collecting samples of specific compounds such as explosives and drugs from surfaces without the use of heat from a sampling probe.

SUMMARY OF THE INVENTION

The invention is an improved method for rapidly checking surfaces for the presence of specific compounds such as trace amounts of explosives. According to the invention a disposable hand-covering, preferably a glove of clean, flexible material such as unbleached cotton, is used to wipe a surface, or two or more surfaces in succession, so as to pick up particles of specific compounds present on the surfaces. After a person wearing the hand-covering wipes various surfaces, particles on the hand-covering are quickly transferred to collector surfaces of a hand-held air sampling probe, preferably a flashlight-sized device containing a battery-powered blower and a coil-shaped collector but not having a heating element. Particles are transferred to and trapped on collector surfaces by positioning the inlet end of the probe near or against portions of the hand-covering which have been in wiping contact with the surfaces being checked, then activating the blower to rapidly draw air and particles through the collector. During particle transfer the probe inlet end is typically rubbed against the palm and at least the tips and front portions of the fingers and thumb of the gloved hand to facilitate removal of particles from all portions of the glove which may contain them.

After particles have been trapped on collector surfaces of the probe, the particles are rapidly analyzed for the presence of explosives or other specific compounds of interest by heating the collector surfaces by an external power source to convert the particles to vapors, then analyzing the vapors. A preferred vapor analysis includes rapidly gas chromatographically-separating the vapors, decomposing selected vapors of the effluent of the gas chromatograph (GC) to form a gas such as nitric oxide, and then detecting the gas. This vapor analysis may be completed in about fifteen to thirty seconds, and acquisition of several samples (by glove wiping of surfaces) and sample transfer from glove to probe may be performed in a time interval of similar length prior to vapor analysis. Hence sample processing rates for the method of the invention can be up to several (e.g., 5–10) samples per minute. Even higher sampling rates are achievable if each vapor analysis is employed to check multiple wipings obtained by two or more persons each wearing a glove (or two gloves). Detection of a predetermined compound such as a specific explosive or drug as a result of this "piggyback" detection sequence is typically followed by individual checking of the objects screened so as to isolate the source of the compound being sought.

DETAILED DESCRIPTION OF PREFERRED EMBODIMENTS

The method of checking surfaces for specific compounds is described below with particular reference to explosives.

Preferred embodiments of the invention have proven of considerable utility in detection of trace amounts of explosives such as the nitramine RDX in its commercial form C-4 on surfaces. However, the emphasis on explosives in the following description is not intended to exclude use of the technique in the detection of other compounds on surfaces; for example, the method may also be of use in checking surfaces for traces of drugs such as cocaine and heroin.

Key steps in a preferred surface-checking technique of the present invention include wiping of surfaces with a suitable hand-covering to pick up small amounts of the explosives; transferring the explosives from the hand-covering to collector surfaces of a sampling probe, and analyzing the explosives trapped on the collector surfaces of the probe. Each of these steps, and preferred materials and instruments used in performing them, are set forth in the following description.

An essential aspect of the surface-checking method is the hand-covering used to wipe surfaces. The hand-covering should satisfy several criteria. To be effective, it must pick up explosives when wiped over surfaces containing small amounts of such compounds in the form of particles. Such particles may, for example, be within fingerprints or films on surfaces or may be attached to dust resting on surfaces. The hand-covering must also be capable of releasing at least some of the particles into a stream of air when vacuumed, unheated, by a sampling probe. The hand-covering must not include releasable materials which will interfere with the detection of explosives. It is also important that the hand-coverings, when vacuumed, not release large amounts of lint or fibers which could plug up the air channels and/or excessively coat the surfaces of the collector within a sampling probe. From the perspective of the user, particularly one performing high volume sampling, the hand-coverings should be comfortable and easy to manipulate. Preferably the hand-coverings are also inexpensive since a fresh, uncontaminated hand-covering is needed once a hand-covering becomes dirty after repeated wipings or after any wiping leads to a detection of explosives.

Figure 1:
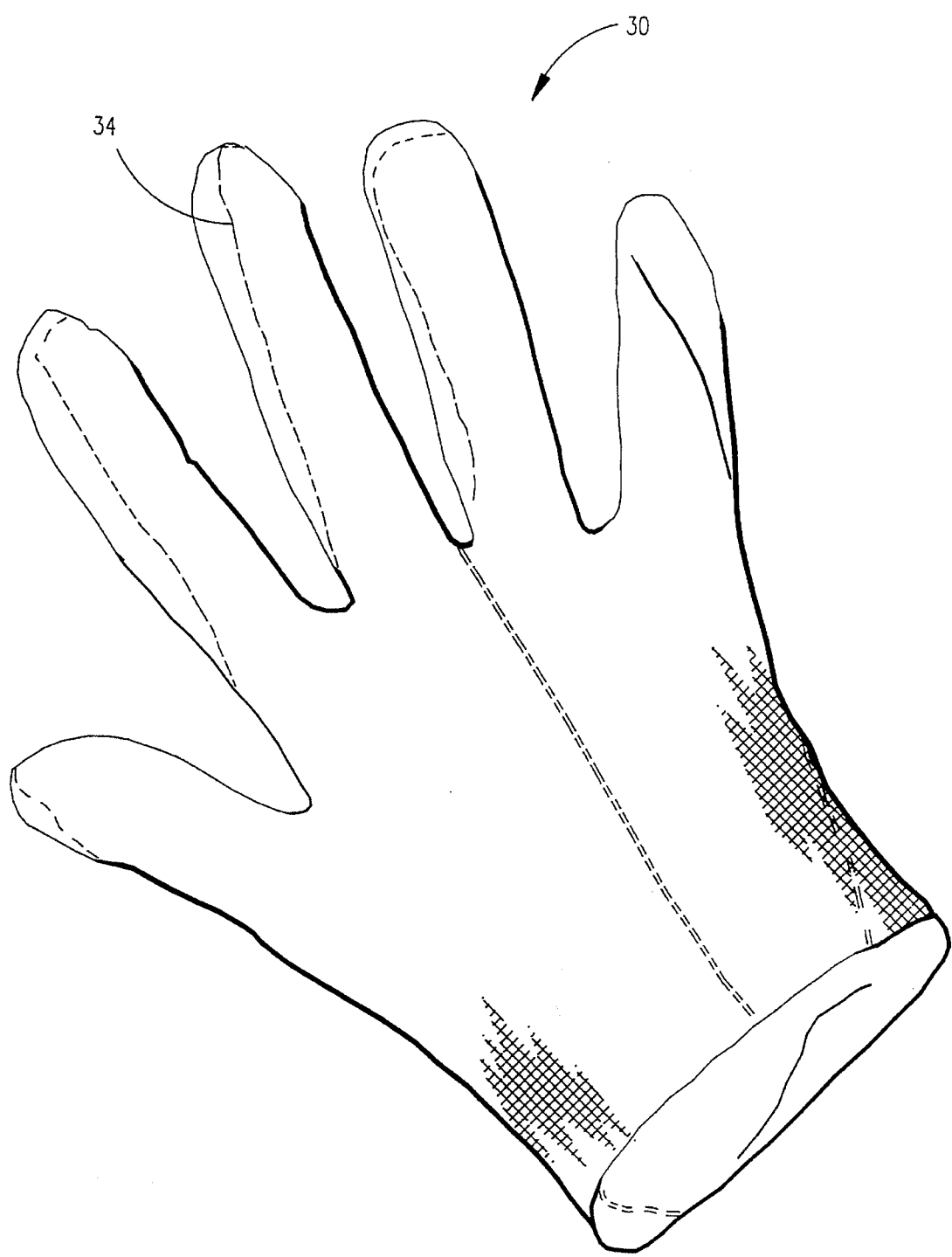
FIG. 1 is a view of a hand-covering suitable for use in wiping surfaces according to a preferred embodiment of the invention.

A preferred hand-covering for use in the surface-checking method of the invention is a five-fingered cotton glove such as the glove 30 illustrated in FIG. 1. The glove which is most preferred at present is an inspection glove formed of 100 percent unbleached cotton lisle available as stock number ADH 633 from the Arnold David Cohen Company of Bedford, Mass. This cotton glove, which is relatively lightweight and soft and fits reasonably closely over the fingers, palm, and back of the user's hand, has been found to yield higher signal peaks and/or fewer interferences with detection of explosives than other hand-coverings evaluated—for example, nylon gloves and mittens of heavier cotton material. Also, these cotton gloves do not shed excessive amounts of lint and hence do not clog collector air passages even after multiple sample transfers. The presence of seams 34 running along the sides and particularly over the fingertips of the cotton inspection glove 30 is also considered desirable. These seams 34 facilitate the application of pressure on surfaces, particularly areas of lesser accessability such as those near gaps formed by adjoining surfaces. The seams 34 may also provide enhanced collectability of explosives due to the local roughness or increased surface area they provide for the glove 30.

A single glove worn by an inspector who is checking surfaces—for example, the exterior surfaces of luggage or of articles removed from luggage at an airport terminal—can be used to wipe several different articles in succession before the materials picked up by the glove are further processed for detection of explosives. Moreover, multiple inspectors or an inspector wearing a glove on each hand, can wipe one or more surfaces with separate gloves whose wipings can be simultaneously analyzed as a single sample. Such "piggyback" sampling allows inspection of a large number of articles or surfaces in a specific time interval; it of course required that the checked articles be segregated or kept track of for subsequent rechecking if explosives are detected during sample analysis.

Figure 2:
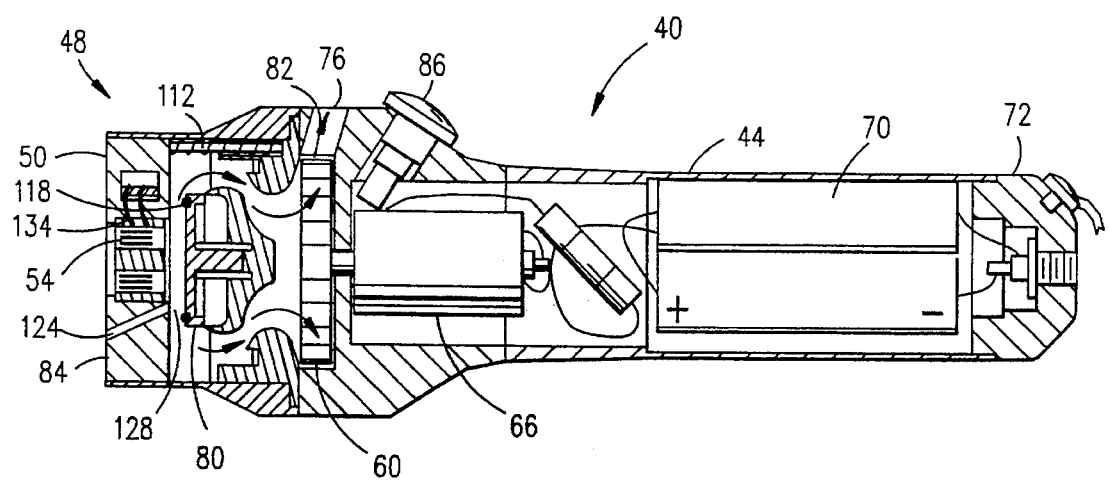
FIG. 2 is a cross-sectional view of a sampling probe suitable for use in the surface-checking method of the invention.

After surfaces have been wiped with an appropriate hand-covering such as the glove 30, particles of explosives held on the glove are quickly transferred to collector surfaces of a hand-held sampling probe. A preferred sampling probe 40, illustrated in cross-section in FIG. 2, is a hand-held device of the size and shape of a standard battery-operated flashlight. The probe 40 includes a generally cylindrical case 44 with an enlarged inlet end 48 within which a collector assembly 50 is mounted. The collector assembly 50 includes a coil 54 resembling in appearance that of an automobile cigarette lighter and having ribbon-like, substantially concentric, windings of a metal such as molybdenum mounted in an annulus—e.g., an annulus that is formed in a cylindrical housing 84 and having an outer diameter of about 0.62 inches and an inner diameter of about 0.38 inches. The windings are coated on one or (preferably) both sides, as with a base layer such as silicon to which there is applied an organic polymer material such the gas chromatographic material DB5 (available from J&W Scientific of Folsom, Calif.). This provides surfaces effective to absorb or otherwise trap particles and vapors of explosives from an air sample drawn unheated through the collector 50, and to release the vapors upon heating of the coatings. Use of a metal substrate for the windings of the collector facilitates electrical resistance heating of the windings to release explosives from the probe 40 for analysis.

Spaced rearward from the collector assembly 50 is an impeller or blower 60 to draw air (and particles of explosives) at a relatively high flow rate (e.g., 3.2 liters/second) through the collector assembly 50 for trapping of explosives on collector surfaces. The blower 60 is driven by a motor 66 which is powered by a battery pack 70 containing one or more (e.g. three) rechargeable batteries accessible through a rear cap 72 of the probe 40. Air drawn through the coil 54 exhausts from the probe 40 through vents 76 spaced about the periphery of the probe case 44 at an axial position at or slightly rearward of the blower 60.

In a manner similar to the vapor sampling probe shown and described in U.S. Pat. No. 4,909,090, the coil 54 is movable between two positions: 1) sample acquisition, and 2) sample desorption. In the sampling position (FIG. 2) the coil 54 is spaced forward of a back seal 80 so that air drawn into the probe 40 and through the coil 54 readily passes around the outer edges of the seal 80 and exhausts from the probe 40 through the vents 76, as indicated by the arrows 82. Thereafter during desorption of the explosives, as described in more detail below, the coil 54 and a housing 84 surrounding the coil 54 are displaced rearward to contact the seal 80 so as to permit flow only in the forward direction through the coil 54.

A preferred method for "vacuuming" particles from the glove 30 into the probe 40 for trapping of explosives on the surfaces of the coil 54 is to activate its blower 60 by means of a switch 86 on the outside of the case 44 and to rub or scrub the inlet end of the probe 40 against portions of the glove which have been in wiping contact with surfaces being checked for explosives. Thus the probe may be rubbed in a continuous path up and down successive fingers, over the palm area of the glove, and against the seamed fingertips.

Because the probe 40 has been found to readily collect particles from gloves without any need to heat the gloves; there is no need to provide heating or temperature control mechanisms in the probe. Hence it can be a rather compact device—e.g., about 11 inches in length and about 3½ inches maximum diameter. Also, there is no need to remove the glove from the user's hand prior to vacuuming the glove. Thus a sample may be transferred from the glove 30 to the coil 54 of the probe 40 in just a few (e.g. 5–10) seconds.

In the event that heating of the glove 30 is found to be desirable for certain applications—either because particle transfer is determined to be inadequate for detection of specific compounds in the absence of heat or because such large quantities of particles are transferred by contact with the glove 30 that the coil 54 or other parts of the vapor detector (described below) become clogged or ineffective—then a glove 30 which has been in wiping contact with a surface may be removed and placed on or within a suitable heater. The probe 40 may then be positioned near or in very light contact with the heated glove 30 to draw vapors of the specific compounds through the collector coil 54.

According to the method of the invention, detection of explosives trapped on the surfaces of the collector coil 54 preferably includes heating of the explosives particles to form vapors which are thereafter analyzed. Although various detectors may be utilized for this purpose, a preferred high speed detector of high selectivity and high sensitivity is an EGIS® explosives detector available from Thermedics Inc. or its subsidiary, Thermedetec Inc., both of Woburn, Mass. Among the explosives whose vapors the EGIS unit is capable of detecting at concentrations of one part explosives in $10^{11}$ parts air or lower are the plastic explosives pentaerythritol tetranitrate (PETN) and the nitramine commonly known as RDX. Structure and operation of an EGIS detector are summarized below.

Figure 3:
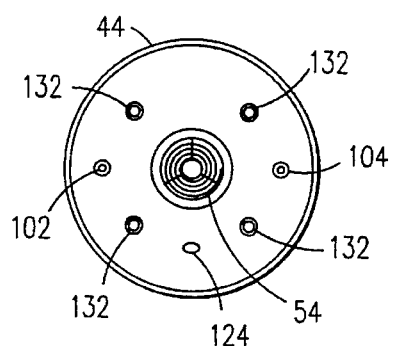
FIG. 3 is a front view of the sampling probe of FIG. 2.
Figure 4:
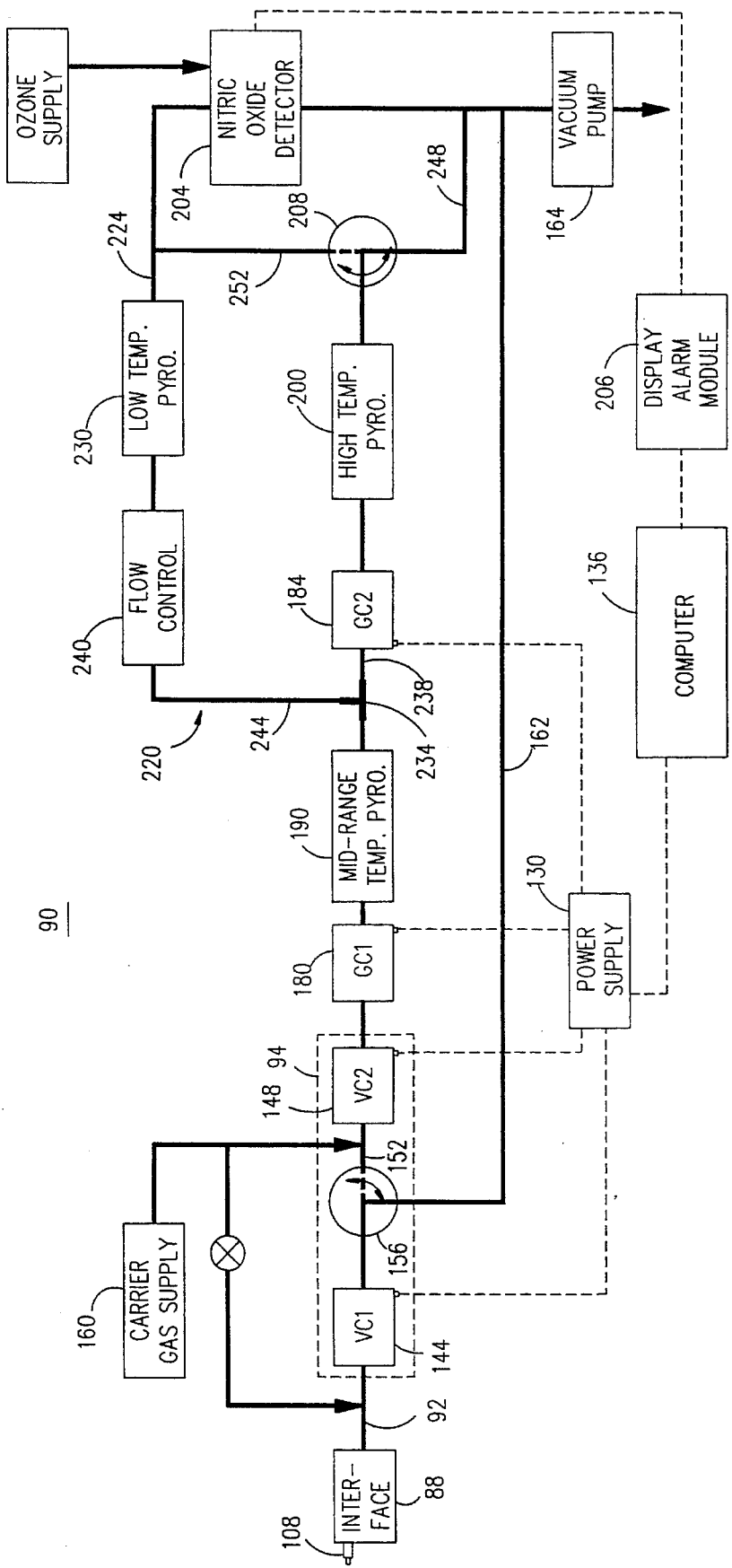
FIG. 4 is a block diagram of a vapor detector suitable for use in the surface-checking method of the invention.

To vaporize the particles of explosives held on the surfaces of the collector coil 54, the windings of the coil are electrically heated while the probe is held by an interface (indicated as item 88 of the vapor detector 90 shown in block diagram form in FIG. 4) which communicates by a flow line 92 to a vapor concentration unit 94. The front face of the probe 40 (FIG. 3) has a pair of alignment holes 102 and 104 which accommodate a pair of pins 108 on the interface 88 (FIG. 4). When the probe 40 is engaged by the pins 108 a pushing motion on the housing 84 surrounding the coil 54 displaces the coil 54 and housing 84 rearward against the action of a spring 112 to a position in sealing contact with an O-ring 118 of the seal 80. With the coil 54 in this rearward position, pressurized air or other gas from the vapor detector 90 is directed through a desorption gas passage 124 in the housing 84 to a space 128 between the seal 80 and the rear of the coil 54 and then out through the coil 54. While air is backflushing the coil 54, the metal windings of the coil 54 are rapidly heated to a controlled temperature by an electrical power supply 130 (FIG. 4) of the vapor detector 90 which is electrically connected to the interface 88 and to the coil 54 through contacts 132 (FIG. 3) and wires 134 and is operated under control of a computer 136. Heating vaporizes and desorbs the explosives particles held on the coated surfaces of the coil 54 and the desorbed vapors are carried into the vapor concentration unit 94.

With reference now to FIG. 4, a summary of the structure and operation of the preferred vapor detector 90 for analyzing explosives wiped from surfaces will now be presented. It should be noted that the vapor detector 90, including the several components illustrated in block diagram form in FIG. 4, is typically housed within a mobile cart requiring as its only external input electrical power (internal batteries allow limited use without external power).

The vapor concentration unit 94 which receives explosives vapors from the coil 54 of the sampling probe 40 serves to concentrate and focus the vapors and to rapidly inject the vapors into a high speed gas chromatograph 180 downstream of the unit 94.

The preferred vapor concentration unit 94 comprises two vapor concentrators VC1 144 and VC2 148 connected by a flow line 152 in which a valve 156 is provided. Each of the vapor concentrators VC1 144 and VC2 148 is connected to a carrier gas supply 160 which supplies hydrogen gas to the concentrators. The vapor concentration unit 94 is typically operated by first receiving an air sample with explosives vapors along the inlet flow line 92 into the VC1 144, with the effluent of VC1 144 (air and non-trapped constituents) being passed along an exhaust line 162 to a vacuum pump 164. In this way vapors which are constituents of the air sample are trapped in VC1 144. The valve 156 is then switched to permit flow communication between the VC1 144 and the VC2 148 (of smaller internal volume). Vapors are then flashed from the VC1 144 by an abrupt heating of VC1 144 and are carried by a carrier gas from the supply 160 into the VC2 148 where they are trapped and thus further concentrated.

Preferred vapor concentrators of the vapor detector 90 each include a small diameter tube such as, in the case of VC2 148, a 0.32 mm ID quartz capillary GC tube about 5–10 inches in length and whose inner surface has a thin coating (e.g., 1–3 microns) of a gas chromatographic material such as polymerized silicone (e.g. DB5 available from J&W Scientific of Folsom, Calif.). In effect, each concentrator is a short gas chromatograph tube. The capillary tube is threaded though, or tightly encased in a needlestock metal tube whose outer surface is in thermal contact with a cooled mass. This mass—e.g., a block of metal in thermal contact with a thermoelectric cooler and with the metal tube, but electrically insulated from the metal tube by one or more layers of insulation such as silicone rubber wrapped around the metal tube—normally maintains the metal tube, and hence inner capillary tube, of the vapor concentrator 144 or 148 at or below room temperature (e.g., at a temperature such as about 10° C.) so that the GC coating will trap vapors from gas samples directed through the capillary tube. The outer metal tube is also connected to the electric power supply 130 for controlled, very rapid resistance heating of the metal tube—for example, from about 10° C. to 250° C. in about one second. This very rapid heating, preferably accomplished automatically under programmed control of the computer 136 in which resistance of the tube is continually monitored (from current and voltage measurements) and employed as a feedback parameter in controlling the power applied to the tube to achieve known resistances corresponding to desired temperatures, in turn heats the GC coating within the capillary tube to release or flash the vapors into a flow of carrier gas directed through the capillary tube. Such carrier gas may in certain application be air, a principal advantage of which is its ready availability. However, air has been found less suitable than other gases for analyses of nitrogen-containing compounds requiring high sensitivity, selectivity, and speed because of its impurities and relatively high molecular weight, and because its oxygen content may foster undesirable reactions. Preferred carrier gases are those which are pure, lightweight, and non-reactive with the compounds to be detected or with their thermal decomposition products or with other compounds which are likely to be present in gas samples. Hydrogen, furnished under pressure to the vapor concentrator 144 or 148 from the carrier gas supply 160 is a preferred carrier gas for use in analysis of nitrogen-containing compounds such as explosives. It has been found safe even when flowing (at low pressures) through a chemiluminescence-based NO detector supplied with ozone as one reactant. Helium is also suitable as a carrier gas.

After vapors have been transferred to and trapped within the VC2 148, this vapor concentrator is flash-heated while carrier gas is flowing through VC2 148. Vapors are swept out of VC2 148 without decomposition of compounds of interest, and are rapidly passed or "injected" into a first gas chromatograph 180 (GC1 180). The GC1 selectively retains and separates vapors of specific compounds both from other compounds to be detected and from compounds not of interest.

GC1 180 and a second gas chromatograph 184 (GC2 184) which receives the effluent of GC1 180 after its passage through a mid-range temperature pyrolyzer 190, may have a construction similar to that of the vapor concentrator 144, except they are typically coiled and are substantially longer. Typical lengths of GC1 180 and GC2 184 are two to ten feet. Also, GC1 180 and GC2 184 are preferably maintained at temperatures somewhat higher (e.g., at 80° C. to 120° C.) than the vapor concentrator 144 by ovens (not shown), except for brief intervals when their temperatures are rapidly increased by application of electrical power from the power supply 130 to the metal tubes encasing their GC capillary columns. When the temperature of GC1 180 is "ramped up"—for example from about 95° C. to 300° C. in a 3–4 second interval, vapors which have been retained and are undergoing timewise separation after being received from the vapor concentrator 148 rapidly emerge in separated form from GC1 180 and pass to the mid-range temperature pyrolyzer 190. The same effect is later produced, by controlled heating of GC2 184, on separable vapors which have been received for selective retention and separation in undecomposed form from the mid-range temperature pyrolyzer 190.

The mid-range temperature pyrolyzer 190 may comprise a short (e.g., six-inch) portion of the (capillary tube) flow line between GC1 180 and GC2 184. The pyrolyzer 190, however, is preferably continuously heated to a temperature sufficient to decompose a first set of specific compounds, if present in the vapors contained in a gas sample, without decomposing vapors of a second set of (more thermally stable) compounds. For example, in the detection of certain nitrogen-containing explosives, the mid-range temperature pyrolyzer 190 may be maintained, as by electrical heating, at a temperature of about 400° C. At this temperature, explosives vapors which are nitramines and nitrite esters (compounds having, respectively, N—$NO_2$ or O—$NO_x$ ($x=1, 2$) in their structural formulas—e.g., nitroglycerin (NG), ethylene glycol dinitrate (EGDN), pentaerythritol tetranitrate (PETN), and the nitramines HMX and RDX—readily decompose to produce nitric oxide (NO) gas and nitrogen dioxide ($NO_2$) gas when passed through the pyrolyzer 190 at flow rates of about one cubic centimeter per second. However, explosives of a second set of compounds known as C-nitro compounds (compounds having C—$NO_x$ ($x=1, 2$) in their structural formulas—e.g., dinitrotoluene (DNT) and trinitrololuene (TNT)) and other organic nitrogen-containing compounds such as perfumes, paint residues, etc. which are potential interferents do not decompose when passed through the pyrolyzer tube 190 as vapors in a carrier gas such as hydrogen.

A high temperature pyrolyzer 200, positioned to receive the effluent of GC2 184, may be of a construction similar to that of the mid-range temperature pyrolyzer 190, or may be a quartz or ceramic tube, typically about five to twelve inches in length and having a diameter of about one-eighth inch. The high temperature pyrolyzer 200 is maintained at a temperature in the range of about 800° C. to 1000° C., typically about 850° C., by a heater. At this temperature vapors of the second set of compounds to be detected (e.g., DNT and TNT), as well as the $NO_2$ gas produced by decomposition of vapors in the mid-range temperature pyrolyzer 190, decompose to produce NO when contained in gas samples passed through the high temperature pyrolyzer 200.

Nitric oxide gas produced in either of the pyrolyzers 190 or 200 is monitored in a nitric oxide detection 204 whose inlet is in communication with the outlet of the high temperature pyrolyzer 200 through a valve 208. The nitric oxide detector 204 may be any suitable highly sensitive, high speed NO analyzer such as a detector using principles of electron capture, photoionization, or chemiluminescence. A preferred NO detector 204 is an ozone-based chemiluminescence detector similar to those used in Thermal Energy Analyzers (TEA's) available from Thermedics Inc. of Wildwood Street, Woburn, Mass., U.S.A. in which ozone supplied to a reaction chamber (maintained under vacuum such as 1–10 torr by the vacuum pump 164) reacts with NO in a gaseous sample to produce "excited" $NO_2$. Rapid decay of the "excited" $NO_2$ to $NO_2$ yields radiation detectable by a photodetector. The resulting signals and their times of occurrence permit identification of specific compounds (e.g., explosives) to be detected. Timewise plots or chromatograms of these signals may be automatically generated and alarms triggered in a display/alarm module 206 connected between the NO detector 204 and the computer 136.

The series-connected, dual GC-pyrolyzer combinations of the vapor detector 90 permit time-shifting of signals by delaying production (and hence detection) of NO gas from a second set of separable compounds which do not decompose when passed through the mid-range temperature pyrolyzer 190 but do decompose when (later) passed through the high-temperature pyrolzyer 200. This permits NO signals from nitramines and nitrite esters to be generated and appear in a first interval of time prior to the decomposition of other compounds retained in, or slowly migrating through, GC2 184.

The second time interval of detection is initiated by the shifting of the valve 208 and the ramping up of the temperatures of GC2 184. Decomposition of these compounds (e.g., C-nitro compounds such as TNT) in the high temperature pyrolyzer 200 results in generation of additional NO signals in the NO detector 204 in a second interval of time.

The time-shifting of signals provided by the vapor detector 90 is of considerable utility in high speed selective detection of compounds such as explosives since it reduces, for each time interval, the number of signals among which specific compounds must be identified or distinguished. It also increases the separation between certain signals of interest. For example, specific compounds (nitramines, nitrite esters) whose signals appear in the first interval of time are not masked by signals of other compounds which are time-shifted into the second interval of time.

The vapor detector 90 preferably also includes a bypass branch 220 which avoids background noise and possible interferences that could appear in the output during the first time interval of detection as a result of reactions in the high temperature pyrolyzer 200. The bypass branch 200 diverts a portion of the effluent of the mid-range temperature pyrolyzer 190 so that it bypasses the second gas chromatograph GC2 184 and the high temperature pyrolyzer 200. Gases and vapors directed through the bypass branch 200 and which then pass to the nitric oxide gas detector 204 along a flow line 224, because they avoid the high temperatures of the pyrolyzer 200 contain decomposition products only of the mid-range temperature pyrolyzer 190 (as further reacted in the low temperature pyrolyzer 230 of the bypass branch 220). Interferences associated with reaction products of the high temperature pyrolyzer 200 are absent, and the vapor detector 90 also achieves detection times comparable to those of a system without the bypass branch 220.

Diversion of a portion of the effluent of the mid-range temperature pyrolyzer 190, which includes vapors contained in a carrier gas, to the bypass branch 220 may be accomplished by a simple "T" connection 234 in the flow line 238 between GC2 180 and the mid-range temperature pyrolyzer 190 and the operation of a flow controller 240 communicating with the T 234 through a flow line 244. The flow controller 240 helps regulate the fraction (e.g., 0.7) of effluent of the pyrolyzer 190 which passes through the bypass branch 220, and may be merely a coiled capillary tube providing a fixed amount of flow resistance. Alternatively, the controller 240 comprises a valve whose setting may be varied so as to allow different amounts of gas flow through the bypass branch 220.

The low temperature pyrolyzer 230 provided as part of the bypass branch 220 functions primarily to reduce to nitric oxide (NO) any $NO_2$ gas in the effluent received from the mid-range temperature pyrolyzer 190. (This function is also performed by the high temperature pyrolyzer 200 with respect to $NO_2$ gas in a sample passing through the pyrolyzer 200.) A suitable low temperature pyrolyzer 230 is a tube formed of, or containing, silver and operable at a temperature in the range of about 140° C. to 200° C.—e.g., at 180° C. A preferred low temperature pyrolyzer 200 comprises a silver tube about twelve inches in length and having an inner diameter of about 0.075 inches and an outer diameter of about one-eighth inch.

The vapor detector 90 of FIG. 4 is operated to provide 1) a first time interval of detection in which NO produced in the mid-range temperature pyrolyzer 190 (and also produced by reduction of $NO_2$) is detected as NO in the nitric oxide detector 204 and 2) a second time interval of detection in which NO produced in the high temperature pyrolyzer 200 is detected in the nitric oxide detector 204. To control the flow of sample gas to the NO detector 204, the valve 208 downstream of the high temperature pyrolyzer 200 is set so that during the first time interval flow of effluent from the high temperature pyrolyzer 200 passes only to the vacuum pump 164 along a flow line 248. Hence NO signals from the nitric oxide detector 204 represent NO produced only by decomposition of nitramines and nitrite esters in the mid-range temperature pyrolyzer 190 (and NO from reduction of $NO_2$ by the low temperature pyrolyzer 230). At the end of the first time interval the valve 208 is rapidly switched. Effluent of the high temperature pyrolyzer 200 is then fed along a flow line 252 to combine with effluent of the low temperature pyrolyzer 230 to pass to the nitric oxide detector 204, which detects NO during the second time interval.

The result of the above-described operations by the vapor detector 90 is rapid, highly selective detection in a time interval of about thirty seconds or less, of one or more explosives acquired by wiping from a surface which may contain very small amounts of the explosive. For example, the explosives nitroglycerin, EGDN, PETN and RDX, if present, are detected during the first time interval while DNT and TNT, if present, are detected in the second time interval.

In the practice of the invention, one or more surfaces to be checked for explosives are wiped with the glove 30, with care being used to contact all portions considered likely to contain traces of explosives. The glove 30 is then held in contact with, and rubbed against, the sampling probe 40 for a short time e.g. 5–10 seconds, while the probe draws unheated air at a high flow rate through its collector coil 54. (If desired, fingertips of the glove 30 may then also be held above the inlet of the probe and rubbed together so to dislodge additional particles for passage into the probe 40. Particles of explosives are thus rapidly transferred from the glove 30 to the coil windings, whose surface coatings trap and hold the explosives. After one or more gloves are vacuumed, the probe 40 is attached to the interface of the vapor detector 90, and the explosives are removed from the probe and analyzed. In the preferred vapor detector 90, rapid resistance heating of the coil windings, along with the back-flushing of the coil with air, desorbs and transfers the explosives, primarily as vapors, to the vapor concentration unit 94. Then, during a time interval of less than thirty seconds, the vapors are GC-separated, pyrolyzed and analyzed for the presence of specific explosives.

FIGS. 5–10 are chromatograms from tests conducted with the explosive RDX using various wiping materials to pick up RDX from outer surfaces of a metal briefcase. The RDX had been applied by dragging a piece of RDX material along the surfaces and/or by handling of the surfaces by a person who had previously handled the RDX material. Other tests on RDX were conducted by wiping surfaces of electronic devices such as cameras and tape recorders. RDX is one of the more difficult explosives to detect by vapor analysis due to its low vapor pressure.

Figure 5:
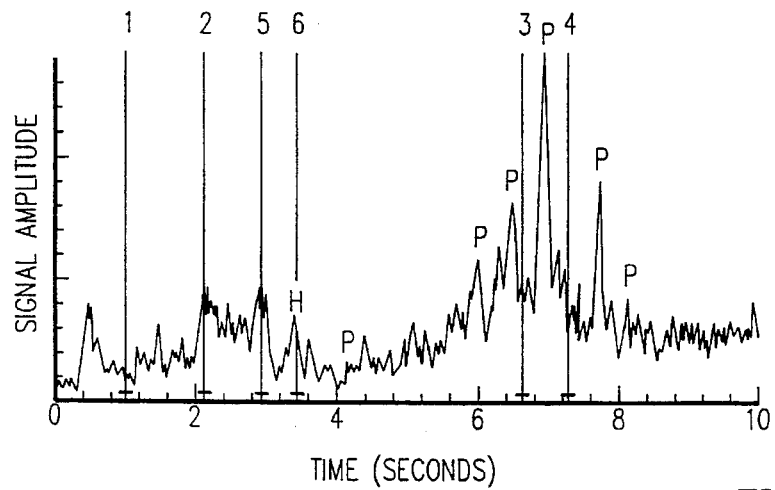
FIGS. 5–7 are chromatographs of signals obtained in tests of an explosive wiped from surfaces by hand-coverings of different materials.
Figure 6:
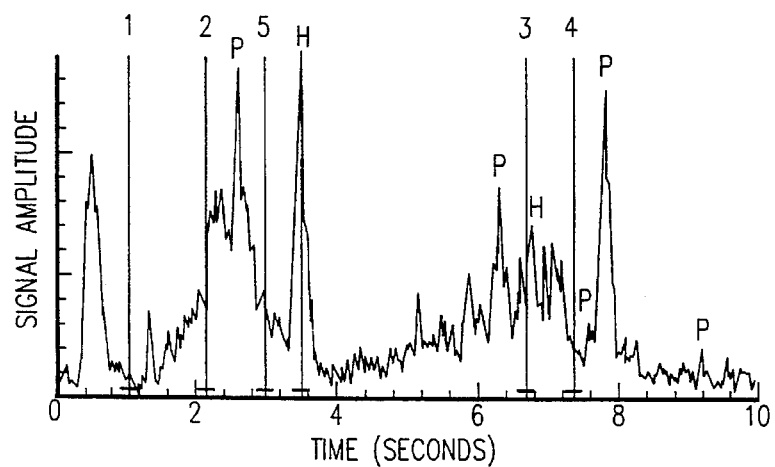
Figure 7:
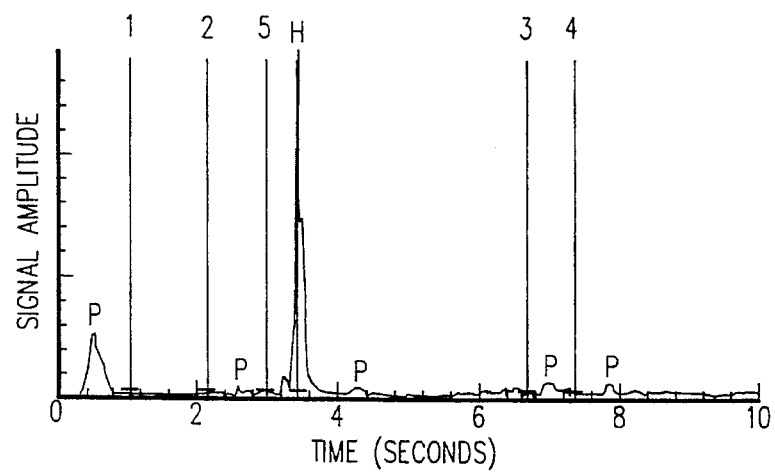

FIGS. 5–7 are chromatograms of signals obtained in tests of the explosive RDX wiped from a surface with hand coverings of different material and processed according to the method of the invention. The plots display signal amplitude versus time over a detection interval of about ten seconds, with the numbered vertical lines corresponding to the pre-determined times at which various explosives should appear if present in a sample. That is, a peak signal of at least a minimum size at the same time as that of a vertical line, or within a time interval or "window" represented by the short horizontal segment (near time axis) on which vertical line is centered, indicates a "hit" or detection of the specific explosive. For the plots given, line 6 corresponds to RDX, the explosive known to be present in the detection tests conducted. Lines 1, 2, 3, 4, 5 correspond, respectively, to times at which EGDN, NG, DNT, TNT, and PETN would be detected if present.

FIG. 5 shows results of tests conducted using a mitten of heavy cotton. The chromatogram has a small peak at the number 6 line, indicating that the mitten may be only marginally effective in detecting RDX. Moreover, this mitten produced a large peak ("P") between lines 3 (DNT) and 4 (TNT), a characteristic signal of the mitten which in other tests yielded false alarms for DNT or TNT. Also, this mitten released large amount of lint during tests, eventually obstructing flow of air through the collector coil of the sampling probe during vacuuming of the mitten.

FIG. 6 is a chromatogram from a sample of RDX obtained from a nylon glove. It illustrates a clear hit for RDX, the explosive present (note "H" at line normally designated as line 6). However, the chromatogram also shows a false alarm for DNT (line 3), an explosive which was not provided for the test, as well as numerous other peaks (e.g., see peak between lines 2 and 5) which could produce interferences if small shifts occurred.

FIG. 7 is a chromatogram from a sample of RDX obtained from an inspection glove of 100% unbleached cotton lisle. The clear "hit" at line 6 indicates detection of RDX, and the absence of other peaks of significant size demonstrates a low probability of interference with detection of any of the five explosives corresponding to the lines 2–6.

Figure 8:
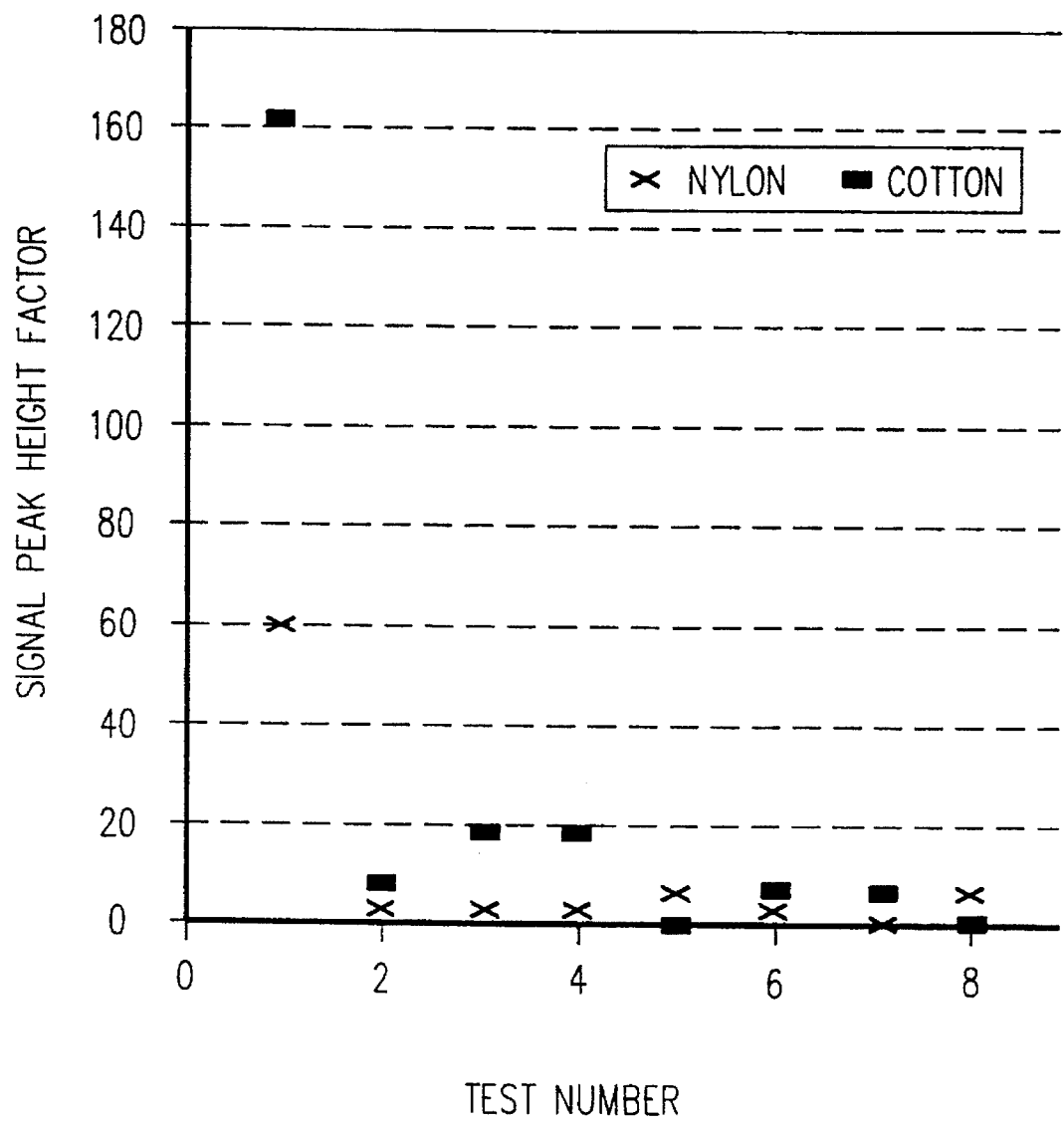
FIG. 8 is a plot illustrating relative peak height of signals obtained in tests of samples of an explosive obtained from gloves of different materials.

FIG. 8 is a plot of the relative peak height of detection signals of RDX obtained from wipings of surfaces made by cotton gloves and nylon gloves in several test runs under similar test conditions. The results show that in six of the eight test runs peak heights for cotton gloves exceeded those for nylon gloves, suggesting a clear advantage of cotton gloves over nylon gloves in detecting low levels of RDX.

Figure 9:
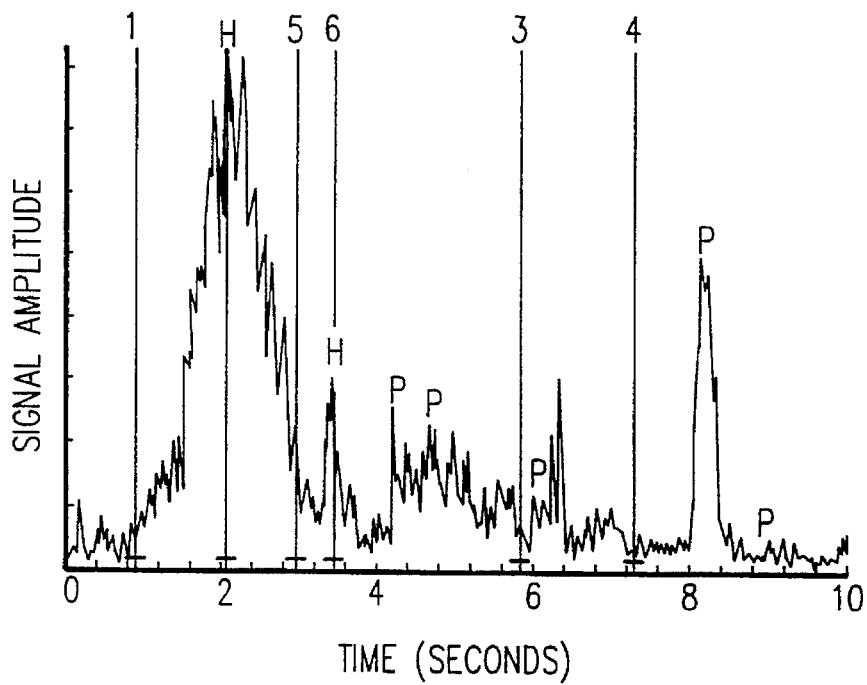
FIGS. 9 and 10 are chromatograms of signals obtained in tests of explosives obtained from surfaces by wiping with materials other than hand-coverings.
Figure 10:
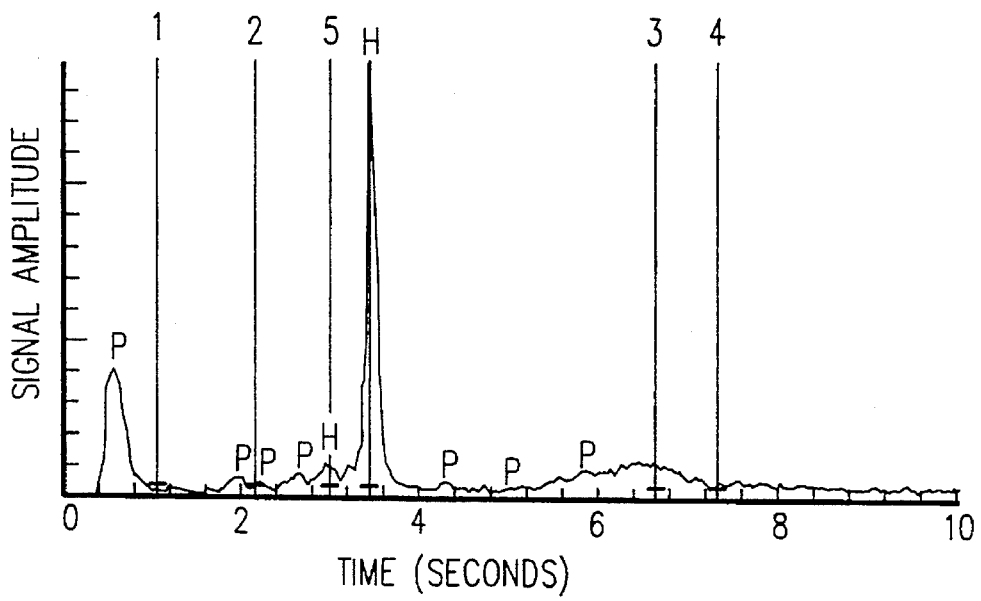

Results of tests with wiping materials other than hand-coverings are shown in FIGS. 9 and 10. In those tests the explosive RDX was wiped from a surface by a paper towel (FIG. 10 results) or a low-lint spec-wipe material commonly used in clean-room applications (FIG. 9 results) and then the towel or spec/wipe was transferred to, and held by, a bail structure for vacuuming by a probe (for paper towel tests, the probe described in U.S. Pat. No. 4,909,090 was used—without, however, the addition of heat). FIG. 9 indicates that the spec/wipe acquired and transferred RDX (note hit at line 6) but also produced a false alarm for nitroglycerin (line 2). FIG. 10 shows that the paper towel was effective and relatively interference-free for RDX detection (the PETN hit at line 5 is believed to be due to contamination of RDX material resulting from storage of the RDX with other explosives in a locker before the RDX was applied to the surface to be wiped). A primary disadvantage of paper towels relative to an effective hand-covering such as a cotton glove, however, is the inconvenience of using the former, particularly in high throughput situations.

The above-described application of the method of the invention relative to explosives is intended to be illustrative and non-limiting. The invention is defined by the claims which follow and includes all embodiments and their equivalents within the scope of the claims.

What is claimed is:

1. A method for rapidly checking surfaces for the presence of trace amounts of nitrogen-containing explosives, including the "plastic" explosives pentaerythritol tetranitrate (PETN) and the nitramine RDX, or nitrogen-containing drugs including the drugs cocaine and heroin, and for identifying the specific explosives or drugs which are present on such surfaces without interference from other substances, comprising:

covering a hand, to be utilized in sample collection, with a hand-covering of material which is flexible, and capable of picking up by wiping and releasably holding particles of nitrogen-containing explosives and drugs from residues on impermeable surfaces left by fingers or hands of persons who have handled such explosives or drugs, and which, when subject to vacuuming, does not release appreciable amounts of (a) lint or fibers or (b) substances which could interfere with accurate detection of said nitrogen-containing explosives and drugs;

wiping a surface which may contain said nitrogen-containing explosives or drugs with the hand-covering so as to transfer particles of said nitrogen-containing explosives or drugs from the surface to the hand-covering;

positioning a sampling probe adjacent to a portion of said hand-covering which has been in wiping contact with said surface while maintaining said probe and said hand-covering in contact or in close proximity, rapidly drawing air over collector surfaces within said probe in a manner to transfer particles or vapors of said nitrogen-containing explosives or drugs from the hand-covering to said collector surfaces without removing from the hand-covering appreciable amounts of (a) lint or fibers or (b) substances which could create interferences with detection of said nitrogen-containing explosives or drugs;

analyzing materials trapped on said collector surfaces, said analysis including heating said collector surfaces to release vapors of said nitrogen-containing explosives or drugs and then detecting said nitrogen-containing explosives or drugs in the vapors, and said handcovering being a glove consisting essentially of unbleached cotton lisle.

2. A method as in claim 1 wherein said hand-covering is a five-fingered glove consisting essentially of unbleached cotton lisle and having seams along the sides and tips of its fingers, and said wiping step includes wiping at least the seamed tips of said fingers over said surface.

\* \* \* \* \*